(12) United States Patent
Tanner

(10) Patent No.: US 11,950,963 B2
(45) Date of Patent: Apr. 9, 2024

(54) PROTECTIVE SHIELD ASSEMBLY

(71) Applicant: Cary Tanner, Fresno, CA (US)

(72) Inventor: Cary Tanner, Fresno, CA (US)

( * ) Notice: Subject to any disclaimer, the term of this patent is extended or adjusted under 35 U.S.C. 154(b) by 530 days.

(21) Appl. No.: 17/244,832

(22) Filed: Apr. 29, 2021

(65) Prior Publication Data

US 2021/0338362 A1 Nov. 4, 2021

Related U.S. Application Data

(60) Provisional application No. 63/026,710, filed on May 18, 2020, provisional application No. 63/017,565, filed on Apr. 29, 2020.

(51) Int. Cl.
*A61B 90/00* (2016.01)
*A61B 90/57* (2016.01)

(52) U.S. Cl.
CPC ............. *A61B 90/05* (2016.02); *A61B 90/57* (2016.02); *A61B 2090/571* (2016.02)

(58) Field of Classification Search
CPC ... A61B 90/05; A61B 90/57; A61B 2090/571; A61B 46/20; A61B 46/00; A61B 46/23; A47F 10/06; A47F 2010/065; E04H 15/34; E04H 15/04
USPC ...................... 160/369, 370; 433/25; 128/897
See application file for complete search history.

(56) References Cited

U.S. PATENT DOCUMENTS

| | | | | |
|---|---|---|---|---|
| 1,378,904 A | * | 5/1921 | Schuermann | G03B 15/06 248/161 |
| 4,445,859 A | * | 5/1984 | Hoffmeister | A61G 15/16 433/79 |
| 4,936,318 A | * | 6/1990 | Schoolman | A61G 13/108 15/301 |
| 5,012,852 A | * | 5/1991 | Blackhurst | B25H 1/20 D24/232 |
| 5,127,830 A | * | 7/1992 | Sheridan | A61G 15/16 433/79 |
| D349,577 S | * | 8/1994 | Sayles | D29/100 |
| 5,335,651 A | * | 8/1994 | Foster | A61G 7/0528 5/503.1 |
| 5,349,967 A | * | 9/1994 | Tennis | A61M 5/00 132/73 |
| 5,360,018 A | * | 11/1994 | Chen | A61B 90/05 128/849 |

(Continued)

OTHER PUBLICATIONS

Canelli, Robert, M.D. et al., "Barrier Enclosure during Endotracheal Intubation", The New England Journal of Medicine, published Apr. 3, 2020 at NEJM.org, retrieved Jul. 13, 2021.

*Primary Examiner* — Beth A Stephan
(74) *Attorney, Agent, or Firm* — Marcus N. DiBuduo; John R. Aaron

(57) ABSTRACT

A shield assembly for protecting against airborne droplets and other fluids, particularly excreted from humans. The shield assembly may generally comprise a shield, one or more support plates or members, a stand, and, optionally, a frame for holding the shield. The shield can be pivotally engaged with the stand, allowing a user of the shield assembly to change the pitch of the shield. The shield assembly may be engaged with a medical table, bed, or gurney, or alternatively may be engaged with a portable, moveable base. A user may position the shield assembly such that the shield thereof is disposed between the user's face and a source of airborne droplets or fluids.

24 Claims, 18 Drawing Sheets

(56) References Cited

U.S. PATENT DOCUMENTS

| | | | | |
|---|---|---|---|---|
| D355,036 S | * | 1/1995 | Shufelt | D24/232 |
| 5,396,904 A | * | 3/1995 | Hartigan, Jr. | A61B 46/27 |
| | | | | 128/853 |
| 5,579,797 A | * | 12/1996 | Rogers | A45B 23/00 |
| | | | | 135/96 |
| 5,865,182 A | * | 2/1999 | Chen | A61B 90/50 |
| | | | | 128/849 |
| 5,947,428 A | * | 9/1999 | Ohl | A61G 5/10 |
| | | | | 248/118 |
| 6,405,742 B1 | * | 6/2002 | Driscoll | A45B 17/00 |
| | | | | 135/42 |
| D613,971 S | * | 4/2010 | Matus, Jr. | D6/699.4 |
| 8,267,147 B2 | * | 9/2012 | Lockwood | A61C 19/00 |
| | | | | 248/104 |
| 9,516,958 B1 | * | 12/2016 | McAllister | A47F 10/06 |
| 9,723,935 B1 | * | 8/2017 | McAllister | A47F 10/06 |
| 10,030,407 B1 | * | 7/2018 | Beedle | A45B 23/00 |
| 11,049,626 B1 | * | 6/2021 | Ahearn | A61B 90/05 |
| 11,160,339 B2 | * | 11/2021 | McKenzie | A45B 23/00 |
| 2007/0236112 A1 | * | 10/2007 | Williman | A47F 3/12 |
| | | | | 312/140.4 |
| 2008/0088211 A1 | * | 4/2008 | Baumgartner | A47F 10/06 |
| | | | | 312/140.4 |
| 2008/0142058 A1 | * | 6/2008 | Chan | A45B 23/00 |
| | | | | 135/20.1 |
| 2010/0045149 A1 | * | 2/2010 | English | A47B 96/062 |
| | | | | 312/140.4 |
| 2014/0265757 A1 | * | 9/2014 | Scott | A47F 10/06 |
| | | | | 312/137 |
| 2016/0073795 A1 | * | 3/2016 | Matus, Jr. | A47F 10/06 |
| | | | | 312/137 |
| 2016/0331155 A1 | * | 11/2016 | Atkins | F16M 11/10 |
| 2020/0085530 A1 | * | 3/2020 | Sauer | A61B 17/0206 |
| 2020/0187678 A1 | * | 6/2020 | Quinter | A47F 10/06 |
| 2021/0154074 A1 | * | 5/2021 | Shetty | A61G 1/04 |
| 2021/0321885 A1 | * | 10/2021 | Zaugg | A61B 90/40 |
| 2021/0369383 A1 | * | 12/2021 | Pawlowicz | A61B 90/05 |
| 2021/0401651 A1 | * | 12/2021 | Ernstoff | A61G 10/005 |
| 2022/0061950 A1 | * | 3/2022 | Asamarai | A61B 90/05 |
| 2022/0175157 A1 | * | 6/2022 | Matus, Jr. | E05D 5/06 |
| 2022/0409323 A1 | * | 12/2022 | Rodriguez Gutierrez | A61C 19/007 |
| 2023/0078674 A1 | * | 3/2023 | Benjamini | A45D 44/02 |
| | | | | 433/92 |

* cited by examiner

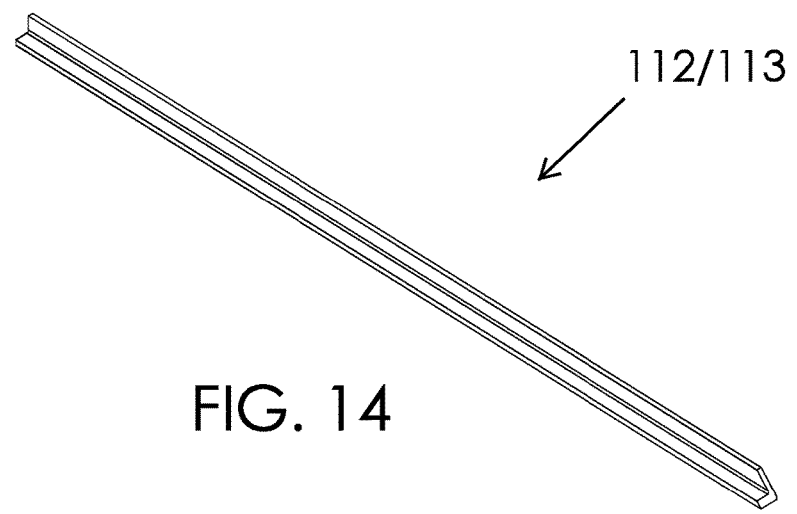
FIG. 14
FIG. 15
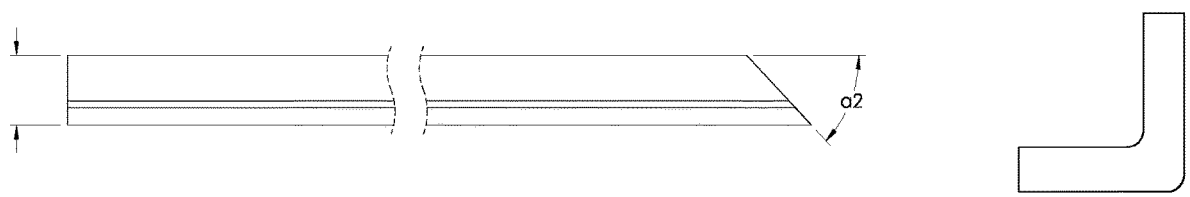
FIG. 16
FIG. 17

PROTECTIVE SHIELD ASSEMBLY

CROSS-REFERENCE TO RELATED APPLICATIONS

The present application claims priority to, and the benefit of, U.S. Provisional Patent Application No. 63/017,565, filed Apr. 29, 2020, and U.S. Provisional Patent Application No. 63/026,710, filed May 18, 2020, each of which are hereby incorporated by reference in their entirety.

FIELD OF THE INVENTION

The present invention concerns an apparatus for minimizing the spread of airborne droplets. More particularly, embodiments of the present invention concern a shield assembly which protects a user from airborne droplets while in close proximity to a source thereof.

BRIEF SUMMARY OF THE INVENTION

The present invention concerns a shield assembly which may be used as a barrier to airborne droplets or other fluids. The assembly may have a shield, a stand for anchoring the assembly, and, optionally, a frame for holding the shield. In some embodiments, the shield may be made from flexible and transparent material, such as, but not limited to, acrylic plastic, and may be generally formed as a thin plate or sheet. A primary function of the shield may be to allow a user to view a given area while protecting the user from airborne droplets, or other possible contaminants, which may be released within the given area. For example, a doctor (e.g., anesthesiologist), who may be performing an intubation procedure on a patient (or any other procedure where a patient's mouth may be open), may position the shield between their face and the patient's face. This allows the doctor to perform the procedure with full visibility while also maintaining a barrier between themselves and the patient.

According to some embodiments, the frame of a shield assembly may have a plurality of members which may be unitarily formed or engaged together. One or more members may be generally straight and elongate and two or more members may be connected together to form the frame. In some embodiments, the frame may generally comprise a rectangular or square shape, or any other shape. It is to be appreciated, however, that a frame may comprise any number of members which may be engaged directly, or indirectly, with each other. One or more members of a frame may be formed as a solid member and/or may be, in some embodiments, constructed from rolled steel comprising a channel (e.g., L-channel, J-channel, U-channel, etc.). In some embodiments, one or more members may be formed as a tube (i.e., a member having a hollow elongated center).

In accordance with some embodiments, one or more members of a frame may have a first leg and a second leg which may be about perpendicular to each other, forming an "L" shape with one leg oriented toward a center of the frame. To ensure that two or more members of a frame are interconnected without play or overlap, one or more legs of a member may be cut at one or both ends. When the shield is positioned within the frame, the shield may be supported by a leg of one or more members such that the shield may be prevented from falling through opening of the frame. It is to be appreciated, however, that a member of a frame may generally comprise any number and configuration of protrusion(s), leg(s), extension(s), or the like which may support the shield while it is positioned within the frame. In some embodiments, one or more members may extend between two parallel-aligned members to provide support to the shield.

In some implementations, a shield may be positioned within a frame by placing the shield between each member of the frame or by sliding, or inserting, the shield from a side of the frame. In some embodiments, one or more members may be formed as a thin strip or plate, such that a shield may be easily inserted from a side of the frame at which the one or more members are disposed without having to bend the shield. A member may have one or more protrusions or lips (or a relatively small leg) which may require less flexing of a shield when it is inserted from the side that the member is disposed. A protrusion or lip may also help secure the shield once it is fully inserted.

According to some embodiments, one or more members of a frame may include one or more protrusions which may extend inwardly from near an edge of a leg. In some embodiments, a protrusion may be integrally formed with a leg, or secured thereto via a fastener or weld. One or more protrusions may be about parallel to any horizontally oriented legs of any members of the frame, forming a slot therebetween which may help secure the shield by limiting vertical movement thereof. It is to be appreciated that a member of a frame may include any number of protrusions which may extend over any portion of the frame opening and which may also be formed as any shape.

According to some embodiments of the present invention, a frame may be connected, directly or indirectly, with a stand of a shield assembly by engagement with a member of the frame. In some embodiments, a frame may have one or more support members which may be used as a means for engaging the frame with a stand. A support member may have one or more legs which may be engaged with one or more members of the frame. In some embodiments, at one end of a leg, the leg may terminate near a center of a support member which may be adjacent to a center of a member of the frame.

According to some embodiments, a support member may be configured to be engaged to a stand of a shield assembly via a rod, plate, or the like, which may be pivotally or fixedly connected to the stand. To engage a support member, a rod of the support member may be inserted into a pivot of the stand and secured thereto by a fastener. In some embodiments, the pivot may provide a means for changing the pitch or tilt of the frame by allowing it to rotate about a central longitudinal axis which may be aligned with the pivot. According to some embodiments, a stand may have a mechanical actuator, such as a lever arm, to lock a frame in a fixed position.

At a lower end, a stand may be engaged with a bed, table, gurney, or the like, (sometimes referred to hereinafter, collectively, as a "table") in order to anchor a shield assembly at a fixed point. In some embodiments, a plate, or plurality of plates, may be disposed at an end of the stand which may allow the stand to be inserted between a mattress and a frame of a table (e.g., operating table). It is to be appreciated however, that the stand may be adapted to be anchored to other fixed objects, or it may be anchored to a movable base.

In some embodiments of the present invention, at its lower end, a stand may be rotatable relative to its anchoring point, which may allow a user to pivot a frame around the stand. In some embodiments, a handle, lever, rod, or the like may be disposed on a stand and/or frame which a user may grasp and use to pivot the frame. When using a shield assembly, in some implementations, a user may pivot a frame such that it may be positioned directly over a working area (e.g., where a doctor will be performing a procedure). If necessary, the user may also change the pitch or tilt of the frame before and/or during a procedure.

To further protect a user, it is to be appreciated that a shield assembly may be used with one or more gowns, drapes, or other types of coverings. A covering may allow a user to enclose a working area, further limiting the spread of any airborne droplets or contaminants. The opening(s) of a covering(s) may be positioned over a shield so as to not impede the view of the working area. In some embodiments, a user may utilize a laparotomy drape, in which case the user may cut away a portion of the drape which covers the view of the operating area. One or more clips, or the like, may be used to secure one or more coverings in place.

In accordance with some embodiments of the present invention, a shield assembly may comprise a shield, one or more support plates, and a stand. A shield may be generally rectangular with one or more cut-out corners. In some embodiments, a cut-out corner may have a rounded edge, or a cut-out corner may have two edges which may be perpendicular or oblique to each other. A cut-out corner may provide space for a user's arm(s) while maintaining a protective barrier while a shield assembly is in use.

According to some embodiments, a support plate of a shield assembly may comprise a unitary plate which may have a thickness which may be greater than a thickness of a shield. In some embodiments, a support plate may comprise an elongated groove which may be configured to receive a portion of a shield, for example, an edge thereof. In some embodiments, a shield assembly may comprise a pair of support plates, where a shield may secured therebetween. One or more spacers may be disposed in a slot formed between a pair of support plates. A support plate may comprise one or more openings for receiving a fastener (e.g., a bolt) and a shield may comprise one or more corresponding openings for receiving the fastener, which may allow the support plate to be connected and secured to the shield. In some embodiments, a support plate may have a notch formed in a lateral edge.

In some embodiments, a support plate may comprise a rod extending laterally therefrom and away from an edge of a shield which may be connected, or otherwise engaged, to the support plate. As described previously with reference to other embodiments, a rod may be inserted into a pivot of a stand and secured thereto by one or more fasteners. A pivot of a stand may provide a means for changing the pitch or tilt of the frame by allowing it to rotate about a central longitudinal axis. In some embodiments, a mechanical actuator, such as a lever arm, may be engaged with the pivot to lock the shield in a fixed position. A lever arm may allow for rapid locking and release of a shield in order to quickly and easily change the pitch of the shield. In some embodiments, a pivot fastener and/or lever arm may be coupled with a spring. In some embodiments, a spacer may be coupled with a pivot fastener and may be disposed between a lever arm and a pivot.

In accordance with some embodiments, disposed along a portion of a stand may be a collar which may be provided to prevent or limit vertical movement of a shield assembly. In some embodiments, a collar may generally comprise an opening throughout a longitudinal center which may be configured or adapted to receive a portion of a stand. A lateral opening may be formed in a collar for receiving a fastener, such as a bolt or a screw. In some embodiments, when a collar is secured to a stand, a fastener may abut a portion of the stand, or, alternatively, may be disposed within a groove, channel, or opening, or the like, of the stand.

In some embodiments of the present invention, a portable base may be provided which may allow a user to freely and portably move a shield assembly (i.e., without having to secure the shield assembly to a table, gurney, or other fixed object). A base may generally comprise a plurality of crossbars and/or arms (or more generally, "elongated members") which may be unitarily formed or connected together using a plurality of fasteners and/or welds. In some embodiments, one or more crossbars and/or arms may be oriented in an upright position and may be configured to be engaged with a stand of a shield assembly. According to some embodiments, an arm may be disposed at or near a top of, and orthogonally to, an upright-oriented member for engaging a stand of a shield assembly. In some embodiments, a base may comprise one or more hinges engaged with one more elongated members, which may allow for an elongated member to be pivoted at a hinge.

In some embodiments, a rail may be engaged to an arm (or other elongated member) to which a clamp may be attached. A clamp may receive a portion of a stand of a shield assembly and secure the stand within the clamp. In some embodiments, one or more tabs may be provided on a rail which may limit or prevent movement of a clamp along the rail. In some embodiments, a clamp may allow a stand to be pivoted and/or rotated. For example, a shield (engaged with a stand) may be pivoted from a position generally orthogonal to a rail of a base, to a position generally parallel with the rail.

One or more crossbars of a base may form a bottom portion (i.e., the portion of the base closest to a reference point, such as the ground). In some embodiments, a bottom portion may generally be arranged in a "U" shape. In some embodiments, a bottom portion may be generally arranged in an "H" shape. It is to be appreciated, however, that a base may comprise any number and configuration of elongated members which may be generally arranged according to any shape. A bottom portion of a base may be generally orthogonal to one or more upright-oriented members. In some embodiments, a bottom portion may have one or more wheels attached thereto. In some implementations, a user may move a shield assembly attached to a base without having to detach and reattach the shield assembly from and to, respectively, gurneys, tables, or other fixed objects.

In accordance with some implementations, a shield assembly may also be used with a table, bed, or gurney, or the like (and which may be movable or fixed). In some embodiments, a shield assembly may be engaged with a medical table using a clamp. For example, a shield assembly may be engaged with a medical table by engaging a clamp 300 with a rail of the medical table, inserting a portion of a stand of the shield assembly into the clamp, and tightening the clamp until the stand is secured therein.

According to some embodiments of the present invention, a shield assembly may comprise: i) a shield; ii) a first support plate which may be engaged with a first side of the shield and a second support plate which may be engaged with a second side of the shield; iii) a stand which may comprise a pivot; iv) a rod which may be engaged with the first support plate and may be pivotally engaged with the stand; and v) a lever arm which may be engaged with a fastener; wherein a portion of the shield may be disposed between the first support plate and the second support plate, wherein the fastener may be disposed through an opening in the pivot and an opening in the rod, and wherein the shield may be rotatable around a first axis centrally aligned with the opening of the pivot.

In some further embodiments, the shield assembly may comprise a clamp which may be configured for engaging the shield assembly to a medical table and wherein a portion of the stand may be received in an opening of the clamp.

In some further embodiments, the stand may be pivotally engaged with the clamp. In some further embodiments, the shield may be pivotable around a second axis centrally aligned with the opening of the clamp.

In some further embodiments, the stand may be pivotable around a third axis orthogonal to the second axis.

In some further embodiments, the shield assembly may comprise a collar and a portion of the stand may be received through an opening in the collar.

In some further embodiments, the shield may comprise a first cut-out and a second cut-out, wherein the first cut-out and the second cut-out may each be formed in a corner of the shield.

In some further embodiments, a portion of the shield may be disposed between a distal end of the first support plate and a distal end of the second support plate, and a lateral edge of the shield may be disposed at about a longitudinal midpoint of each of the first support plate and the second support plate.

In some further embodiments, the second support plate may comprise a notch at a proximal end and may be aligned with the rod.

In some further embodiments, the shield assembly may comprise a slot between the first support plate and the second support plate, wherein the slot may be disposed between a proximal end of each of the first support plate and the second support plate.

In some further embodiments, the shield assembly may comprise a plurality of spacers disposed within the slot.

In some further embodiments, the pivot and the fastener may be coupled with a spring.

According to some embodiments of the present invention, a system for protecting a physician from airborne droplets produced by a patient may comprise: a) a shield assembly which may comprise a i) shield, ii) a first support plate which may be engaged with a first side of the shield, iii) a second support plate which may be engaged with a second side of the shield, and iv) a stand which may comprise a pivot; b) a clamp may comprise a handle, an opening, and a bracket; wherein the first support plate may be pivotally engaged with the pivot of the stand, wherein a portion of the stand may be received within the opening of the clamp, wherein the shield may be rotatable around a first axis centrally aligned with an opening of the pivot, wherein the shield may be pivotable around a second axis centrally aligned with the opening of the clamp, and wherein the stand may be pivotable around a third axis orthogonal to the second axis.

In some further embodiments, the system may comprise a medical table and the shield assembly may be engaged with the medical table by the clamp.

In some further embodiments, the medical table may comprise a rail and the bracket of the clamp may be connected to the rail.

In some further embodiments, the system may comprise a portable base and the shield assembly may be engaged with the base by the clamp.

In some further embodiments, the base may comprise a rail and the bracket of the clamp may be attached to the rail.

In some further embodiments, the base may comprise one or more tabs for limiting the movement of the bracket along the rail.

In some further embodiments, the base may comprise a plurality of elongated members.

In some further embodiments, the base may comprise a hinge and at least one of the elongated members may be pivotally engaged with the hinge.

In some further embodiments, the shield assembly may comprise a collar and a portion of the stand may be received through an opening in the collar.

In some further embodiments, the elongated members may comprise an arm, a medial crossbar, a first upright crossbar, a second upright crossbar, a first lateral crossbar, and a second lateral crossbar, wherein the arm may be connected to the medial crossbar, wherein the first upright crossbar and the second upright crossbar may each be connected to the medial crossbar, wherein the first lateral crossbar may be connected to the first upright crossbar, and wherein the second lateral crossbar may be connected to the second upright crossbar.

In some further embodiments, the base may comprise a plurality of wheels engaged with at least one of the elongated members.

According to some embodiments of the present invention, a shield assembly may comprise: i) a shield which may comprise a first cut-out and a second cut-out; ii) a first support plate which may be engaged with a first side of the shield and a second support plate which may be engaged with a second side of the shield, wherein a portion of the shield may be disposed between the first support plate and the second support plate and wherein a lateral edge of the shield may be disposed at about a longitudinal midpoint of each of the first support plate and the second support plate; iii) a stand which may comprise a pivot, wherein the pivot may comprise an opening and wherein the shield may be rotatable around a first axis centrally aligned with the opening of the pivot; iv) a rod which may be engaged with the first plate and which may be pivotally engaged with the stand; v) a lever arm which may be engaged with a fastener, wherein the fastener may be disposed through the opening in the pivot and an opening in the rod; and vi) a plurality of spacers which may be disposed within a slot between a proximal end of each of the first support plate and the second support plate.

BRIEF DESCRIPTION OF THE DRAWINGS

FIG. 14 is a perspective view illustrating an exemplary side member of the frame illustrated in FIG. 7.

FIGS. 15 and 16 are side views illustrating the side member of FIG. 14.

FIG. 17 is a cross-sectional view illustrating the side member of FIG. 14.

DETAILED DESCRIPTION OF THE INVENTION

The invention, in its various aspects, will be explained in greater detail below. While the invention will be described in conjunction with several exemplary embodiments, the exemplary embodiments themselves do not limit the scope of the invention. Similarly, the exemplary illustrations in the accompanying drawings, where like elements have like numerals, do not limit the scope of the exemplary embodiments and/or invention, including any length, angles, or other measurements provided. Rather the invention, as defined by the claims, may cover alternatives, modifications, and/or equivalents of the exemplary embodiments.

Figure 1:
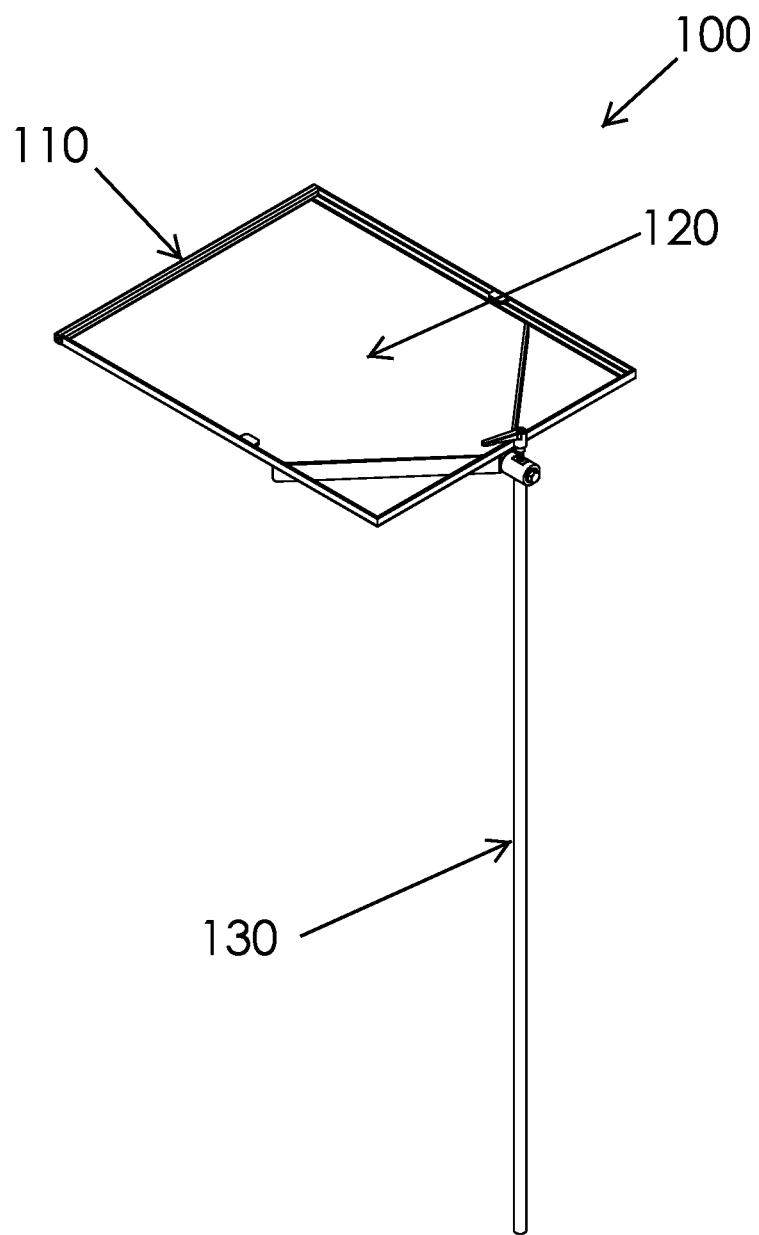
FIG. 1 is a perspective view illustrating an exemplary shield assembly.
Figure 2:
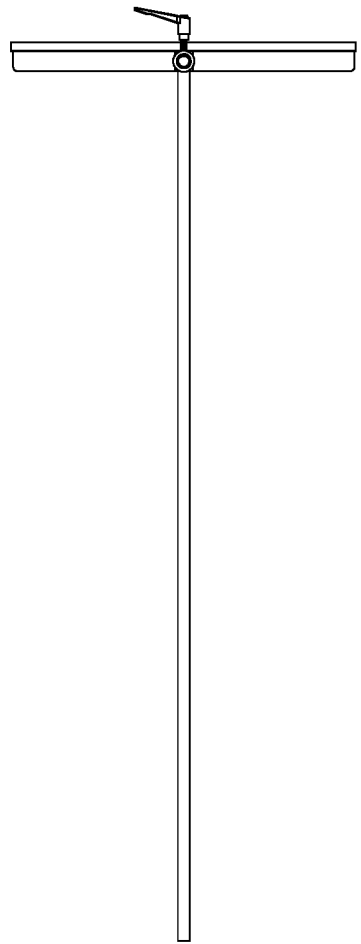
FIGS. 2 and 3 are side views illustrating the shield assembly of FIG. 1.
Figure 3:
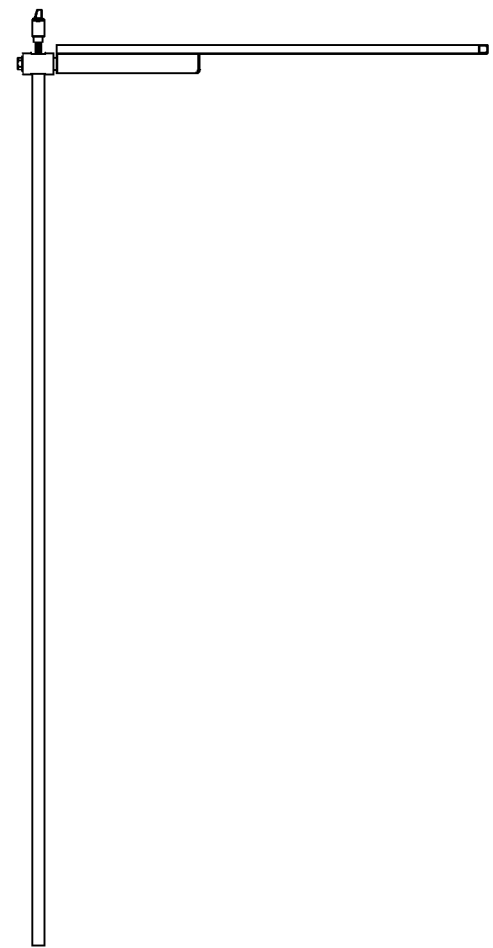
Figure 4:
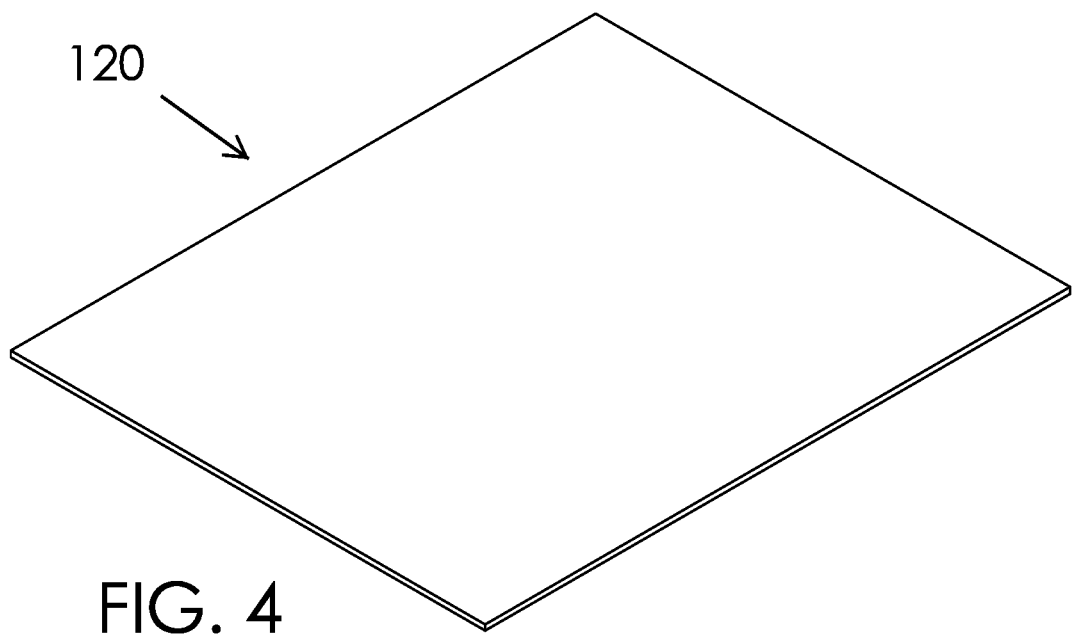
FIG. 4 is a perspective view illustrating an exemplary shield of a shield assembly.
Figure 5:
FIG. 5 is a front (back) view illustrating the shield of FIG. 4.
Figure 6:
FIG. 6 is a side view illustrating the shield of FIG. 4

The present invention generally concerns a shield assembly which may be used as a barrier to airborne droplets or other fluids. In accordance with some embodiments, a shield assembly may generally comprise a shield, a frame, and a stand. For example, referring generally to FIG. 1-3, a shield assembly 100 may include a frame 110, for holding a shield 120, and a stand 130. In some embodiments, a shield may be constructed from flexible and transparent, or semi-transparent, material, such as, but not limited to, acrylic plastic. As illustrated, for example, in FIGS. 4-6, shield 120 may be generally formed as a thin plate or sheet with substantially planar surfaces. As further illustrated in FIGS. 4 and 5, shield 120 may be shaped in accordance with the shape of frame 110 (or vice versa) such that there is little to no play between frame 110 and the perimeter of shield 120.

Figure 7:
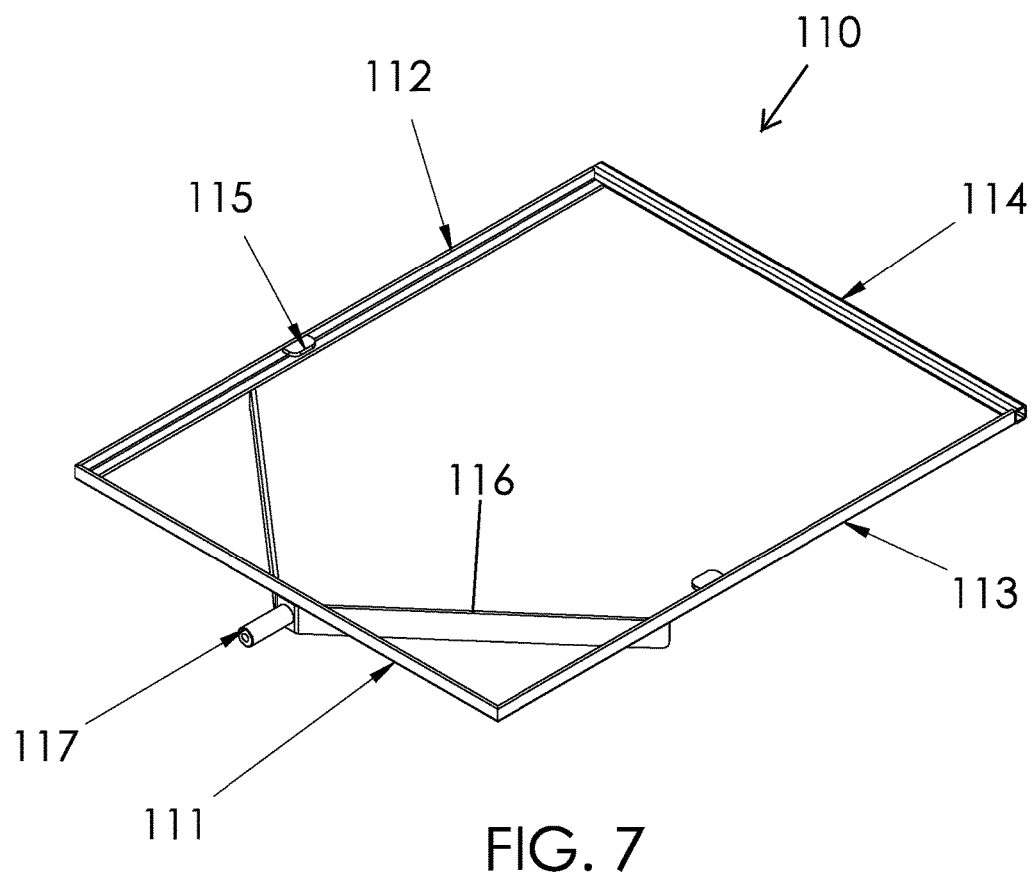
FIG. 7 is a perspective view illustrating an exemplary frame of the shield assembly illustrated in FIG. 1.
Figure 8:
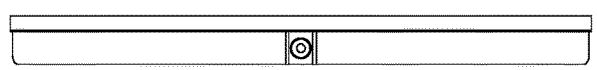
FIG. 8 is a front view illustrating the frame of FIG. 7.
Figure 9:
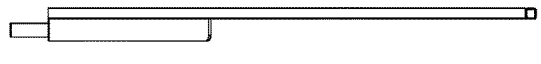
FIG. 9 is a side view illustrating the frame of FIG. 7.
Figure 10:
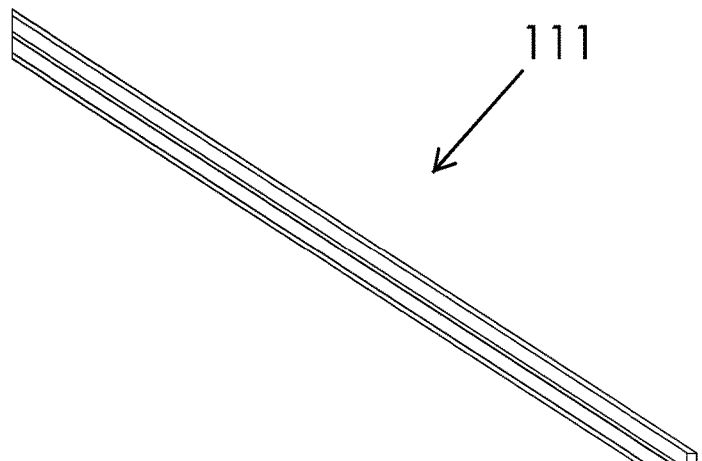
FIG. 10 is a perspective view illustrating an exemplary side member of the frame illustrated in FIG. 7.
Figure 11:
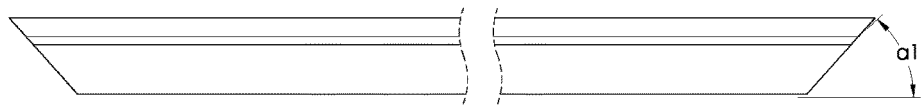
FIGS. 11 and 12 are side views of the side member of FIG. 10.
Figure 12:
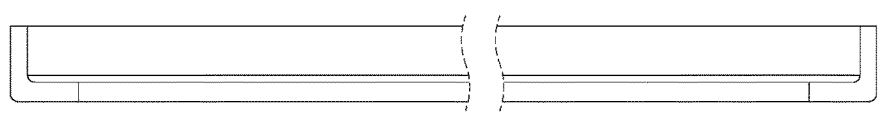
Figure 13:
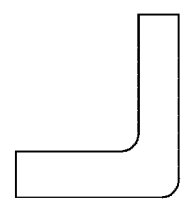
FIG. 13 is a cross-sectional view of the side member of FIG. 10.

In some embodiments, a frame of a shield assembly may comprise a plurality of members which may be unitarily formed or engaged together. For example, as illustrated in FIG. 7, frame 110 may comprise four, generally straight and elongate members—a first side member 111, a second side member 112, a third side member 113, and a fourth side member 114, wherein the members may be engaged end-to-end to form a generally rectangular shape. More particularly, a first end of first side member 111 may be connected to second side member 112 at a first end thereof; a second end of first side member 111 may be connected to third side member 113 at a first end thereof; a first end of fourth side member 114 may be connected to second side member 112 at a second end thereof; and a second end of fourth side member 114 may be connected third side member 113 at a second end thereof. As configured, and according to some embodiments, first side member 111 may be substantially parallel to fourth side member 114 and second side member 112 may be substantially parallel to third side member 113 (and, thus, first side member 111 and fourth side member 114 may each be substantially perpendicular to second side member 112 and third side member 113). It is to be appreciated, however, that a frame may comprise any number of side members which may be detachably connected, welded together, or otherwise engaged via one or more screws, bolts, or the like and which, when engaged together, may form any shape.

Figure 18:
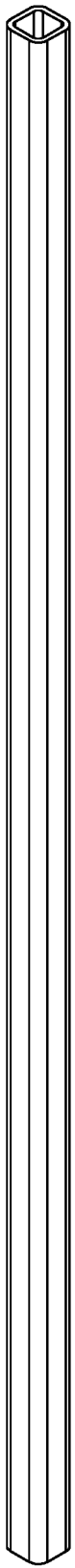
FIG. 18 is a perspective view illustrating an exemplary stand of a shield assembly.
Figure 19:
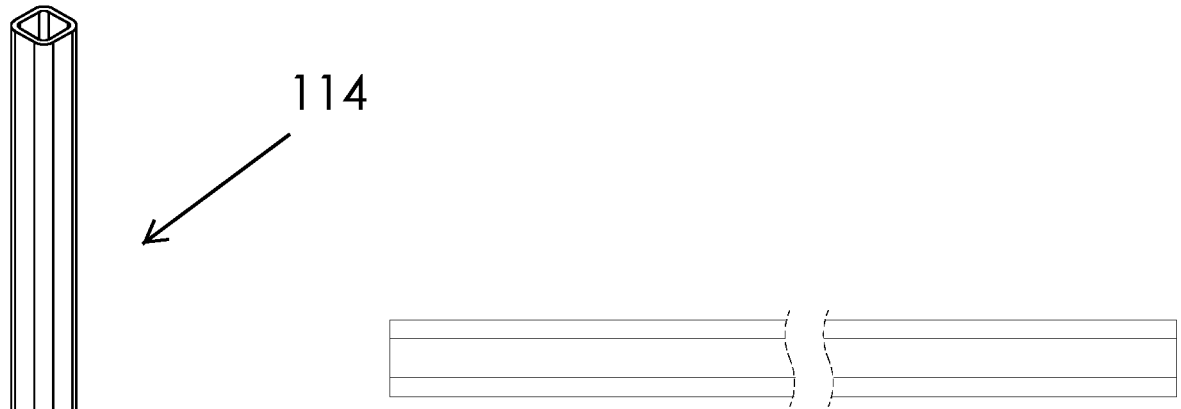
FIG. 19 is a side view illustrating the stand of FIG. 18.
Figure 20:
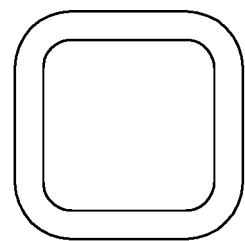
FIG. 20 is cross-sectional view illustrating the stand of FIG. 18.
Figure 21:
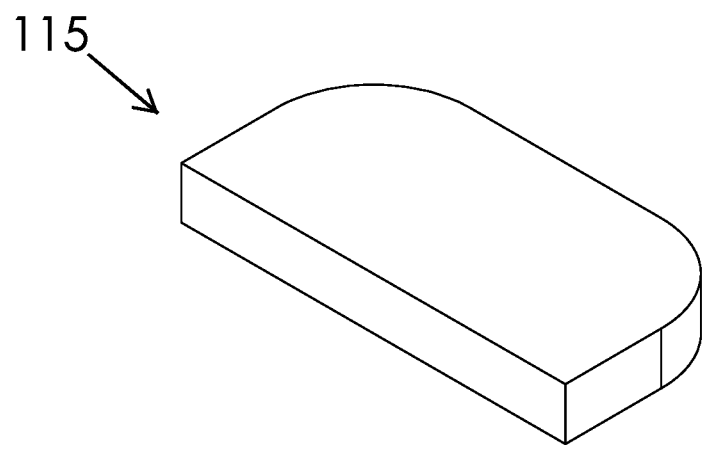
FIG. 21 is perspective view illustrating an exemplary protrusion.
Figure 22:
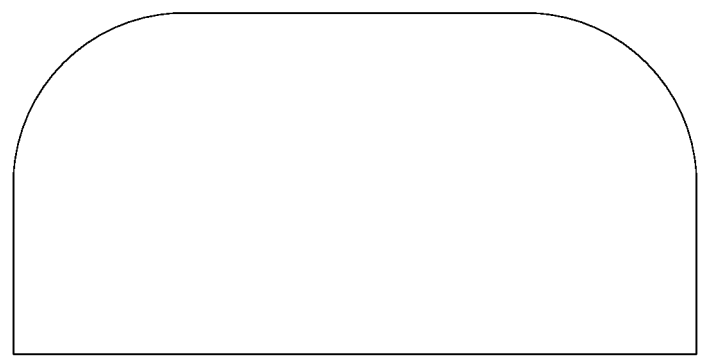
FIG. 22 is a top (bottom) view illustrating the protrusion of FIG. 21.
Figure 23:
FIG. 23 is a side view illustrating the protrusion of FIG. 21.
Figure 24:
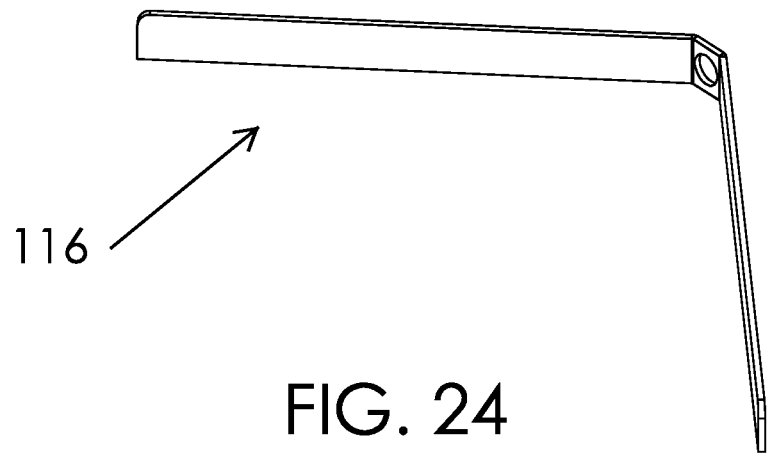
FIGS. 24-27 are perspective, front, top (bottom), and rear views, respectively, illustrating an exemplary support member of the frame illustrated in FIG. 7.
Figure 25:
Figure 26:
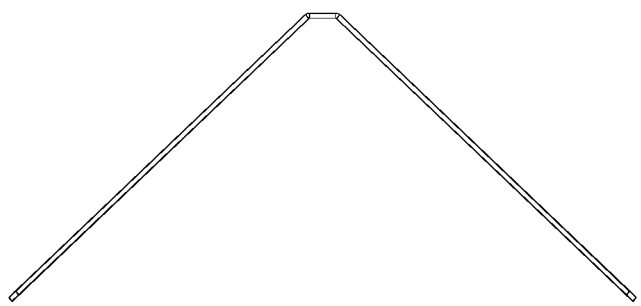
Figure 27:

According to some embodiments of the present invention, one or more members of a frame may be constructed from rolled steel. A member constructed from rolled steel may comprise a hollow elongated opening or a channel. For example, as illustrated in FIGS. 10-13, first side member 111 of frame 110 may be shaped to have an L-channel (i.e., "L"-shaped cross-section). Similarly, and as illustrated in FIG. 14-17, second side member 112 and third side member 113 (which, in some embodiments, may be interchangeable) of frame 110 may also be shaped to have an L-channel. It is to be appreciated, however, that a member of a frame may comprise any type of channel including, but not limited to, a J-channel, a U-channel, or a C-channel. In some embodiments, a member may be formed as a tube. For example, as illustrated in FIGS. 18-20, fourth side member 114 of frame 110 may comprise a square tube (i.e., having an elongated hollow center with a generally square cross-sectional shape).

In accordance with some embodiments, and as further illustrated in FIG. 7, first side member 111, second side member 112, and third side member 113 may be oriented so that a first leg of each side member is positioned vertically and a second leg of each side member is positioned horizontally and inward (i.e., toward the center of frame 110). To ensure that the side members of a frame are interconnected without play or overlap, in some embodiments, one or more legs of a side member may be cut at one or both ends at a particular angle. For example, as further illustrated in FIGS. 11 and 16, the horizontally positioned leg of first side member 111 may have each of its ends cut at an angle α1 and the horizontally positioned legs of second side member 112 and third side member 113 may have one of their ends (i.e., the end adjacent to first side member) cut at an angle α2. In preferred embodiments, angles α1 and α2 may be about 45 degrees.

As best illustrated in FIG. 7, when shield 120 (not shown) is positioned within frame 110, shield 120 may be supported by the horizontally oriented legs of first side member 111, second side member 112, and third side member 113, such that shield 120 may be prevented from falling through opening of frame 110. It is to be appreciated, however, that a side member of a frame may generally comprise any form of protrusion(s) which may extend inward from the side member to support a shield while it is positioned within the frame. Furthermore, one or more members may extend between two parallel-aligned side members to provide support to a shield. For example, a thin planar member may be connected to, and between, a pair of parallel-aligned side members, wherein a first end and a second end of the thin planar member are connected to the body (i.e., not an end) of a first one and second one of the side members, respectively.

According to some embodiments, a shield may be positioned within a frame by placing the shield between each member of the frame or by sliding, or inserting, the shield from one side of the frame. In some implementations, it may be advantageous to have a side member which may be formed as a thin strip or plate, such that a shield may be easily inserted from the side of the frame that the side member is disposed without having to bend the shield (or limiting the amount of flex thereof). Alternatively, a side member may have one or more protrusions or lips (or a relatively small leg) which may require less flexing of a shield when it is inserted from the side of a frame with the side member, while also helping to secure the shield once it is fully inserted. For example, in some embodiments, a side member may have a protrusion disposed near a center of a surface of a side member which may prevent a shield from sliding or otherwise moving past the protrusion.

In some embodiments, a side member may include one or more protrusions which may extend inwardly (i.e., toward a frame opening or, when positioned therein, the shield) from near an edge of a leg and which may be integrally formed therewith, or secured thereto via a fastener or weld. For example, as illustrated in FIGS. 7 and 21-23, second side member 112 and third side member 113 may each have a protrusion 115, shaped as thin plates with rounded edges, which may overlap a portion of a shield near its edges. In some embodiments, a plurality of protrusions may be substantially parallel to the horizontally oriented legs of the side members and may further secure a shield by limiting vertical movement thereof. In some embodiments, a side member may comprise a U-channel, wherein the legs thereof may support a shield from either side thereof. It is to be appreciated that a side member may include any number of protrusions which may extend over any portion of a frame opening and which may also be formed as any shape, such as, but not limited to, a triangle, square, semi-circle, or semi-oval.

According to some embodiments of the present invention, a frame may be connected with a stand of a shield assembly by the engagement with a side member. For example, a side member may be engaged to a stand via a rod, plate, or the like, which, at one end, may be connected to the body of the side member and, at the other end, may be connected to the body, or other component, of the stand. In some embodiments, a frame may comprise one or more support members which may have one or more legs which may be engaged with a side member. For example, as illustrated in FIGS. 7 and 24-27, frame 110 may comprise a support member 116 with a first leg and a second leg generally forming a "V" shape, with a first end of the first leg and a first end of the second leg engaged with second side member 112 and third side member 113, respectively. At a second end of each of the legs of the support member, the legs may terminate near a center of support member. In some embodiments, a frame may be engaged with the stand of a shield assembly via a support member (see, e.g., FIG. 1). In other embodiments, however, a frame may be directly connected to the stand of a shield assembly.

Figures 28, 29:
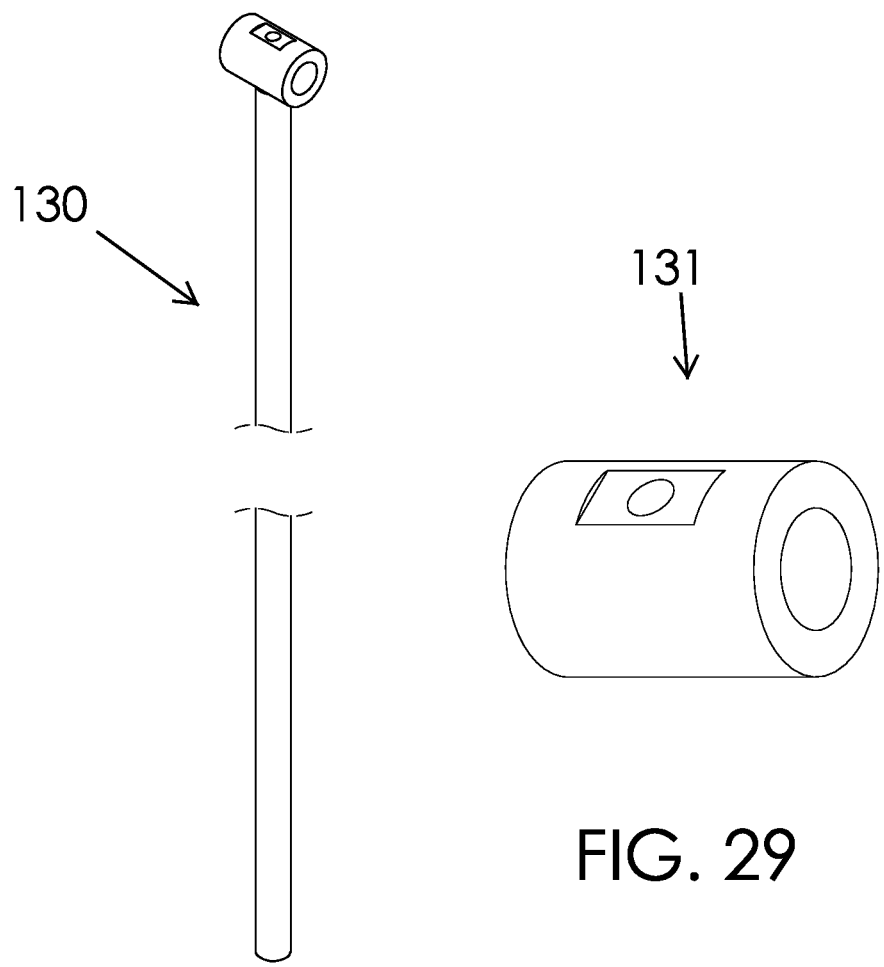
FIG. 28 is a perspective view illustrating an exemplary stand of a shield assembly.
FIG. 29 is a perspective view illustrating an exemplary pivot of the stand illustrated in FIG. 28.
Figure 30:
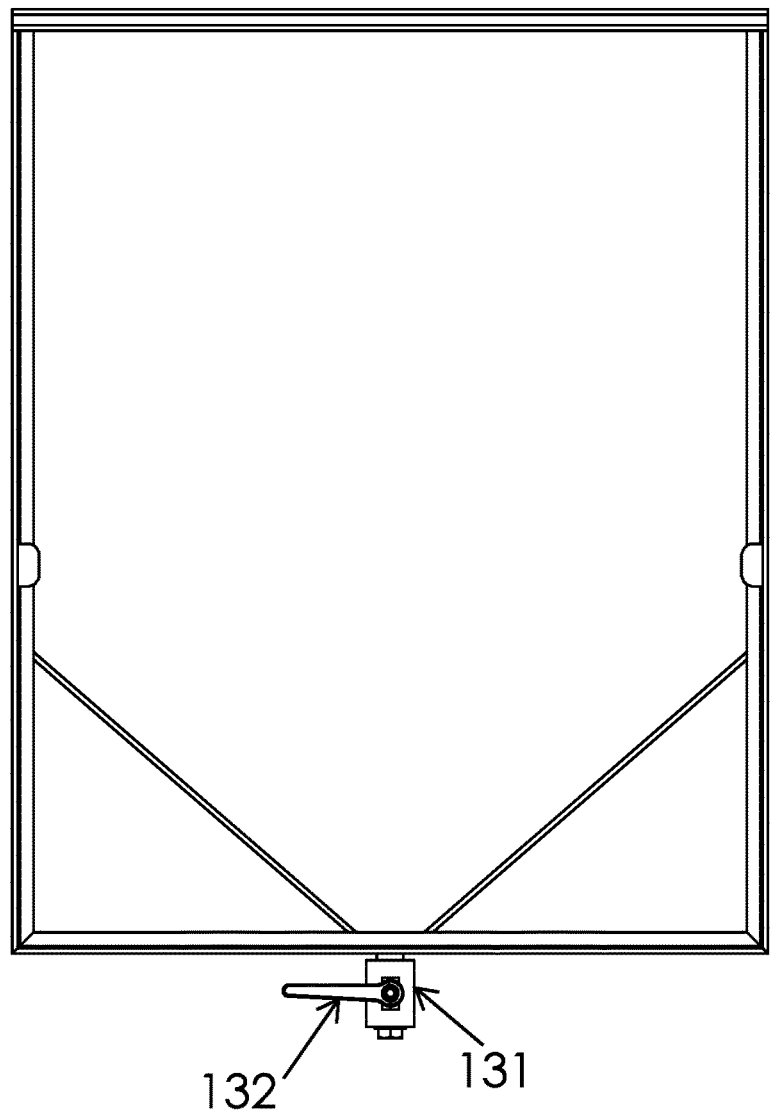
FIG. 30 is a top view illustrating the shield assembly of FIG. 1 with an exemplary lever arm and pivot illustrated at the bottom of the figure.
Figure 31:
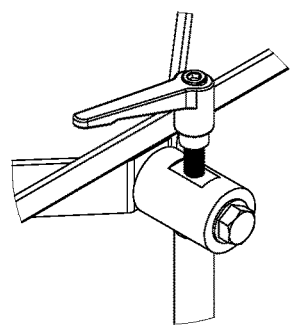
FIG. 31 is a perspective view illustrating the lever arm and pivot of FIG. 30.

In accordance with some embodiments, a support member may be configured to be engaged to a stand via a rod, plate, or the like, which may be pivotally or fixedly connected to the stand. For example, as further illustrated in FIG. 7, support member 116 may be configured to be engaged with stand 130 (not illustrated) via rod 117. According to some embodiments, to engage support member 116 with stand 130, rod 117 may be inserted into pivot 131 of stand 130 (see, e.g., FIGS. 28 and 29) and secured by a fastener (e.g., a bolt) which may be inserted through an opening in rod 117 (see, e.g., FIG. 31). For some embodiments in which a frame may directly engage a stand, a rod may be disposed on a side member (instead of a support member) for insertion into a pivot of a stand. In some embodiments, a rod may be secured by a retractable fastener. A pivot (such as pivot 131 of FIGS. 28-29) may provide a means for changing the pitch of a frame, by allowing the frame to rotate about a central longitudinal axis. In some embodiments, a pivot may be free moving (i.e., lacking a manual means of locking and unlocking the pivot), which may allow a user to adjust the pitch of a frame freely and maintain the desired pitch after any adjustments without having to manually lock the position of the frame. In some implementations, a mechanical actuator (e.g., lever, handle, switch, etc.) may be used to lock the frame in a fixed position or at a desired pitch. For example, as illustrated in FIGS. 30 and 31, stand 130 may have a lever arm 132 which, when disengaged (unlocked), may allow a user to change the pitch of frame 110 by rotating frame 110 around an axis which may be aligned with a center of pivot. When lever arm 132 is engaged (locked), frame 110 may be locked in place, preventing a user from changing the pitch of frame 110. In some embodiments, a mechanical actuator may be used to adjust the tension of the pivot to allow a user to maintain or adjust the pitch of the frame.

In accordance with some embodiments of the present invention, at a lower end, a stand may be engaged with a medical bed, table, gurney, or the like, (sometimes referred to hereinafter, collectively, as a "table") to anchor a shield assembly at a fixed point. For example, at a lower end, a stand may be engaged to a side of an operating table. In some embodiments, a plate, or plurality of plates (which may, for example, generally form a "fork" shape), may be disposed at an end of a stand which may, for example, allow the stand to be anchored by the insertion of the plate(s) between a mattress and frame of a table (e.g., operating table). It is to be appreciated however, that a stand may be adapted to be anchored to other fixed objects, such as a wall or ceiling. In some implementations, a shield assembly may be freestanding, in which a stand may be anchored to, for example, a movable base.

According to some embodiments, at a lower end, a stand may be rotatable relative to its anchoring point, which may allow a user to pivot a frame around the stand. In some embodiments, a handle, lever, rod, or the like may be disposed on a stand or frame which a user may grasp and use to pivot the frame. For example, a T-bar may be disposed at an upper end of a stand which may be used to pivot the frame without having to contact any other portion of the shield assembly.

In preferred implementations, when using a shield assembly, a user may pivot the frame such that it may be positioned directly over a section of a table. If necessary, the user may change the pitch of the frame (e.g., if overhead lighting is causing a glare) before starting, and during, a procedure. By using a transparent shield, during a procedure, a user may be able to clearly see a patient, the user's hands and operating instruments, and any other appendages and instruments which may be involved in the procedure, while maintaining a protective barrier between the user and patient during the entirety of the procedure.

To further protect one's self (as well any surfaces or other persons nearby), in some implementations, a shield assembly may be used in combination with gowns, drapes, or other types of coverings. For example, one or more "U"-shaped adhesive drapes may be applied to a shield and/or frame of a shield assembly to create an enclosure around the shield and/or frame and operating area. The opening(s) of the drape(s) may be positioned over the shield and/or frame so as to not impede the view of the operating area. Alternatively, and in accordance with some implementations, one or more laparotomy drapes may be used to create an enclosure around a shield and/or frame. If needed, a user may cut away a portion of a covering(s) which may otherwise impede the view of the operating area. In some implementations, one or more clips, pins, or clamps, or the like, may be used to secure one or more coverings in place.

Figure 32:
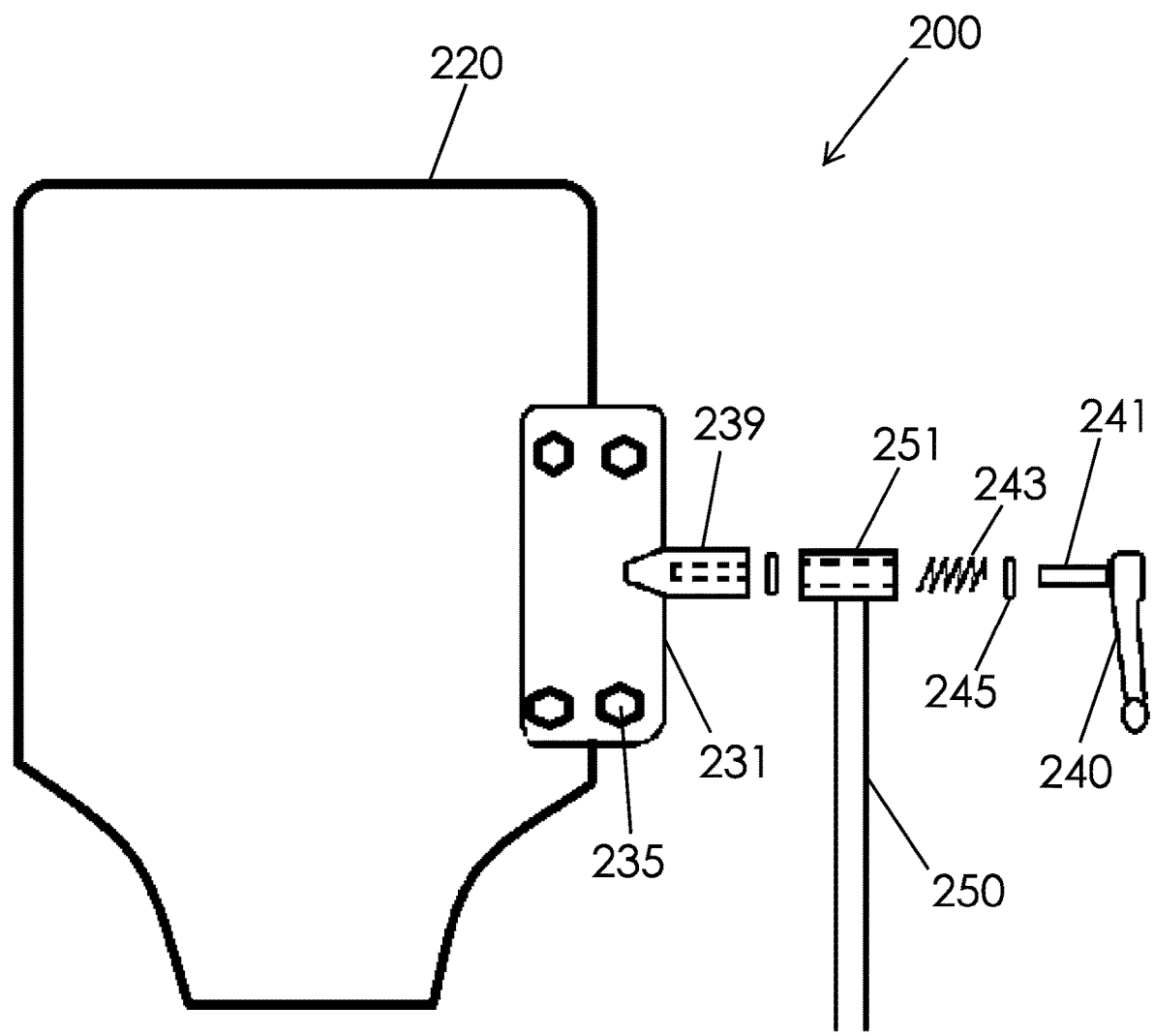
FIG. 32 is a front view illustrating an exemplary shield assembly.
Figure 33:
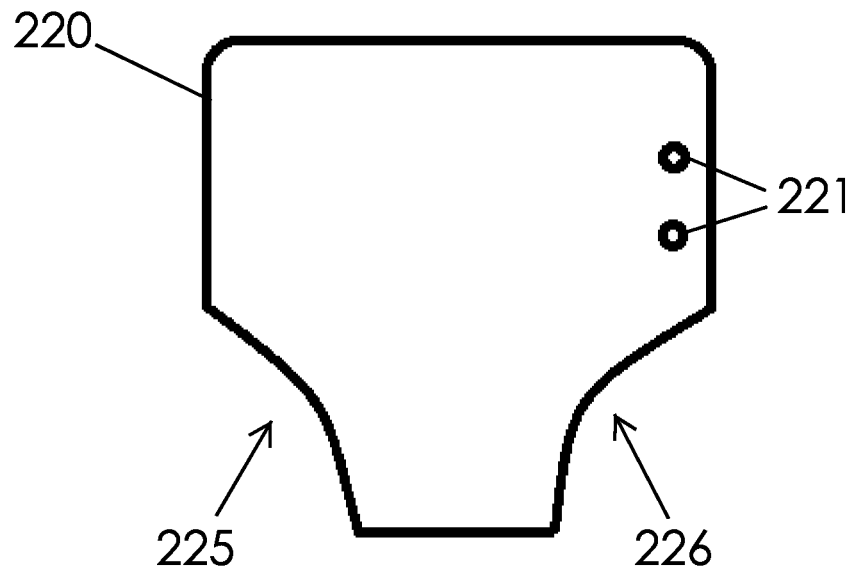
FIG. 33 is a front view illustrating an exemplary shield of the shield assembly illustrated in FIG. 32.
Figure 34:
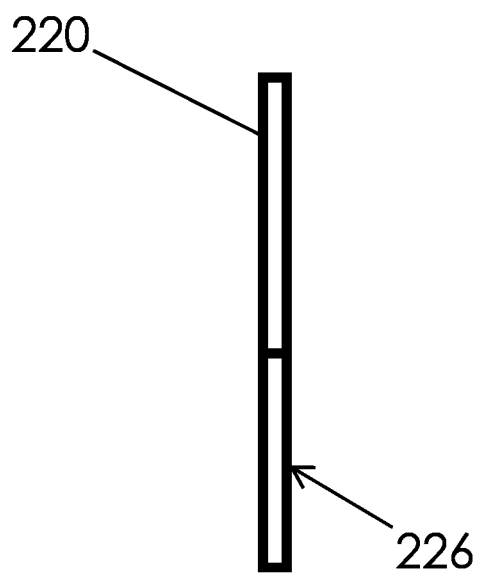
FIG. 34 is a side view illustrating the shield of FIG. 32.

Referring now, generally, to FIGS. 32-44 (and in comparison with FIGS. 1-31), in some embodiments of the present invention, a shield assembly 200 may comprise a shield 220 (i.e., without a frame), a first support plate 231 and a second support plate 232, and a stand 250. A shield may be generally rectangular with one or more cut-out corners or sides. In some embodiments, a cut-out corner may have a rounded edge, or may, alternatively, have two edges oriented oblique or orthogonal to each other. For example, as illustrated in FIG. 33, two adjacent corners of shield 220 may comprise inwardly curved edges, forming cut-outs 225 and 226. It is to be appreciated, however, that a shield may have any number of cut-outs which may comprise any shape or size. For example, and without limitation, a cut-out may be in the form of a circular opening which may be configured to allow a user's hand and arm to pass therethrough.

Figure 35:
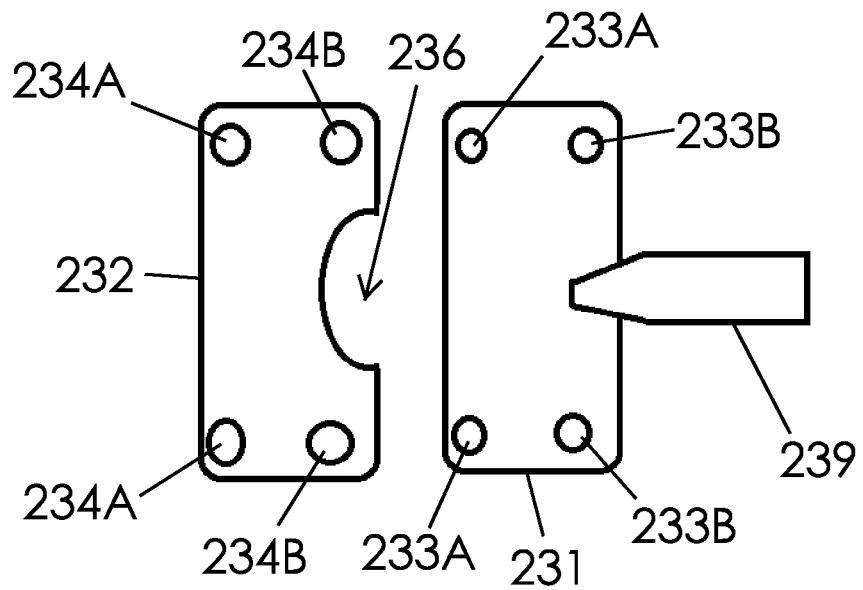
FIG. 35 is a front view illustrating exemplary support plates of the shield assembly illustrated in FIG. 32.
Figure 36:
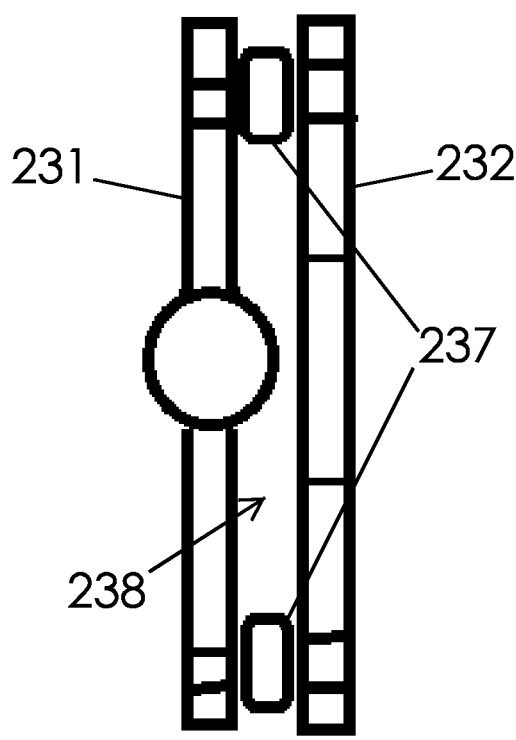
FIG. 36 is a first side view illustrating the support plates of FIG. 35 shown engaged together.
Figure 37:
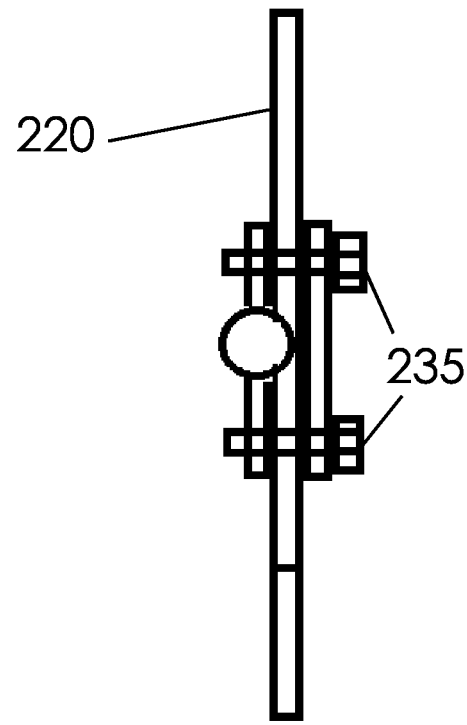
FIG. 37 is a second side view illustrating the support plates of FIG. 35 and the shield of FIG. 34 shown engaged together.

According to some embodiments, a support plate of a shield assembly may comprise a unitary plate which may have a thickness which may be greater than the thickness of a shield. In some embodiments, a support plate may generally comprise a trapezoidal shape. A support plate may, in some embodiments, comprise an elongated groove through which a portion of a shield may be disposed. It is to be appreciated, however, that a support plate may comprise any shape and may be formed as a plurality of plates or pieces. For example, as illustrated in FIGS. 32, 35, and 36, first support plate 231 and second support plate 232 may be provided as a means for securing shield 220 to stand 250. As further illustrated in FIG. 35, and in accordance with preferred embodiments, first support plate 231 and second support plate 232 may generally comprise a rectangular shape. In some embodiments, a support plate may have a notch (or cut-out, slot, or the like) disposed at a lateral edge. For example, as also illustrated in FIG. 35, a notch 236 may be formed in second support plate 232 on a proximal edge (i.e., closest to stand 250) thereof.

In some embodiments, one or more openings may be provided in a support plate and a shield for receiving one or more fasteners, which may allow the support plate to be connected and secured to the shield. As more clearly illustrated in FIGS. 32 and 37, shield 220 may be secured between a distal end (i.e., furthest from stand 250) of first support plate 231 and a distal end second support plate 232, with a lateral edge of shield 220 disposed at about a longitudinal midpoint of each of first support plate 231 and second support plate 232. Shield 220 may have a pair of openings 221 (see, e.g., FIG. 33) near a lateral edge for receiving fasteners 235 (see, e.g., FIGS. 32 and 37), and first support plate 231 and second support plate 232 may have each have a corresponding first pair of openings 233A and 234A, respectively, disposed near a first lateral edge (i.e., closest to shield 220; see, e.g., FIG. 35), for receiving fasteners 235. Disposed near a second lateral edge of each support plate (i.e., closest to rod 239) may be a second pair of openings 233B in first support plate 231 and a corresponding second pair of openings 234B in second support plate 232 for receiving fasteners 235. As most clearly illustrated in FIG. 36, and in accordance with some embodiments, a plurality of spacers 237 may be disposed within a slot 238 between a proximal end of first support plate 231 and a proximal end of second support plate 232.

In accordance with some embodiments, a support plate may comprise a rod extending laterally therefrom. For example, as illustrated in FIGS. 32 and 35, first support plate 231 may comprise a rod 239, wherein a pointed end thereof may be engaged with support plate 231. It is to be appreciated that a rod may comprise any shape and may be integrally formed with a support plate, or connected thereto by one or more fasteners or welds, or the like. Plate rod 239 may be engaged with and/or abut a pivot 251 of stand 250 and may be secured by a pivot fastener 241. As best illustrated in FIG. 32, pivot fastener 241 may be received in an opening in pivot 251 and in an opening in rod 239 (the position of pivot fastener 241, when inserted, being illustrated by broken lines), allowing for rod 239 (and thus shield 220) to rotate relative to stand 250. The engagement of shield 220 with pivot 251 of stand 250 may provide a means for changing the pitch or tilt of shield 220 by allowing it to pivot about a central longitudinal axis which may be generally aligned with an axis passing through a center of the openings in rod 239 and pivot 251.

In some embodiments, and as illustrated, for example, in FIG. 32, a lever arm 240 may be engaged with pivot fastener 241 and may serve as a mechanical actuator to lock shield 220 (and rod 239 and support plates 231 and 232) in a fixed position. In some embodiments, a pivot fastener and/or lever arm may be coupled with a spring. For example, and as further illustrated in FIG. 32, pivot fastener 241 may be coupled with a spacer 245 and/or spring 243. In some embodiments, a pivot fastener may be threaded. In some implementations, spring 243 may be disposed within an opening of pivot 251 and pivot fastener 241 may be received therethrough. In some embodiments, and as illustrated, a spacer 245 may be disposed between pivot 251 and rod 239. In some implementations, a lever arm may allow for rapid locking and release of a shield in order to quickly and easily change the pitch of the shield. It is to be appreciated that other configurations of spacers and/or springs are contemplated in accordance with some embodiments of the present invention. For example, and without limitation, a spring may be disposed between a spacer and lever arm, or between a spacer and a rod. It is also to be appreciated that a pivot fastener may be engaged, or integrally formed, with a rod (instead of, for example, a lever arm).

Figure 42:
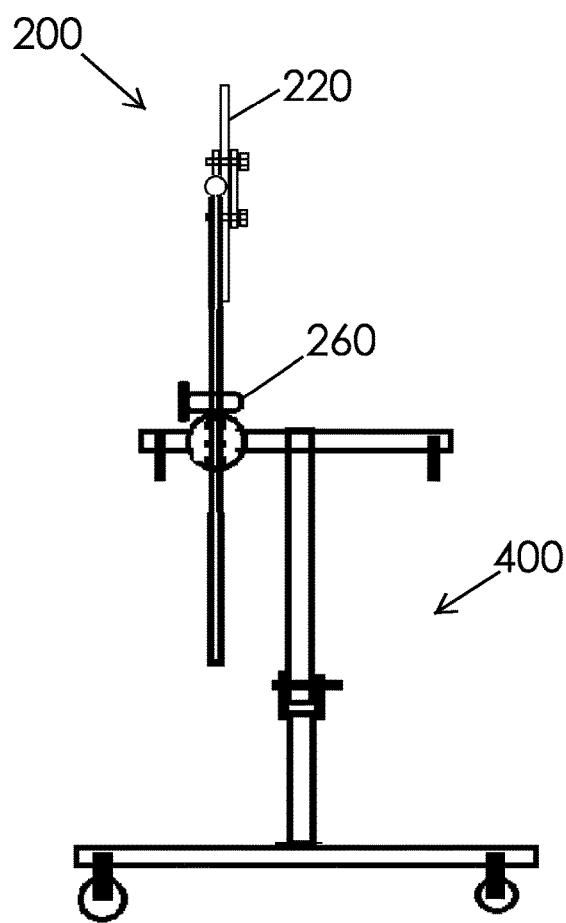
FIG. 42 is a side view illustrating the shield assembly of FIG. 32 engaged with the base of FIG. 38, wherein the shield of the shield assembly is positioned about orthogonally to a rail of the base.
Figure 43:
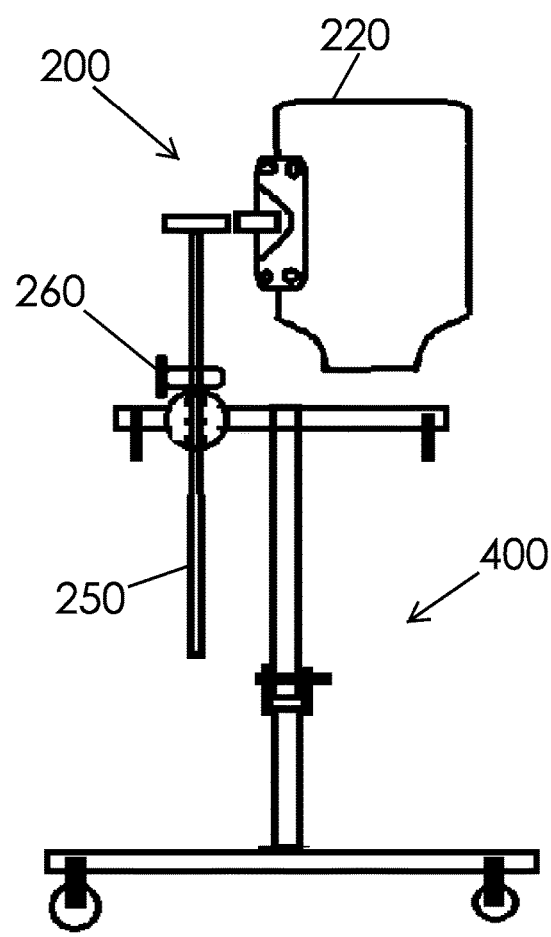
FIG. 43 is a side view illustrating the shield assembly of FIG. 32 engaged with the base of FIG. 38, wherein the shield of the shield assembly is positioned about parallel to the rail of the base.

As illustrated, for example, in FIGS. 42 and 43, disposed along a portion of stand 250 may be a collar 260 which may be provided to prevent vertical movement of stand 250 (e.g., to prevent the shield from inadvertently falling onto a user's hands or arms or onto a patient during an operation). For example, if a stand were to come loose at its attachment point to a table, the collar may impede vertical movement of the stand. According to some embodiments, a collar may be generally circular or cylindrical and may comprise an opening throughout its longitudinal center for receiving the stand. In some embodiments, a lateral opening (i.e., an opening formed along the circumference of a collar) may be formed in a collar for receiving a fastener, such that when the collar is secured to a stand, the fastener may abut a portion of the stand, or may be disposed within a groove, channel, or opening, or the like, of the stand.

Figure 38:
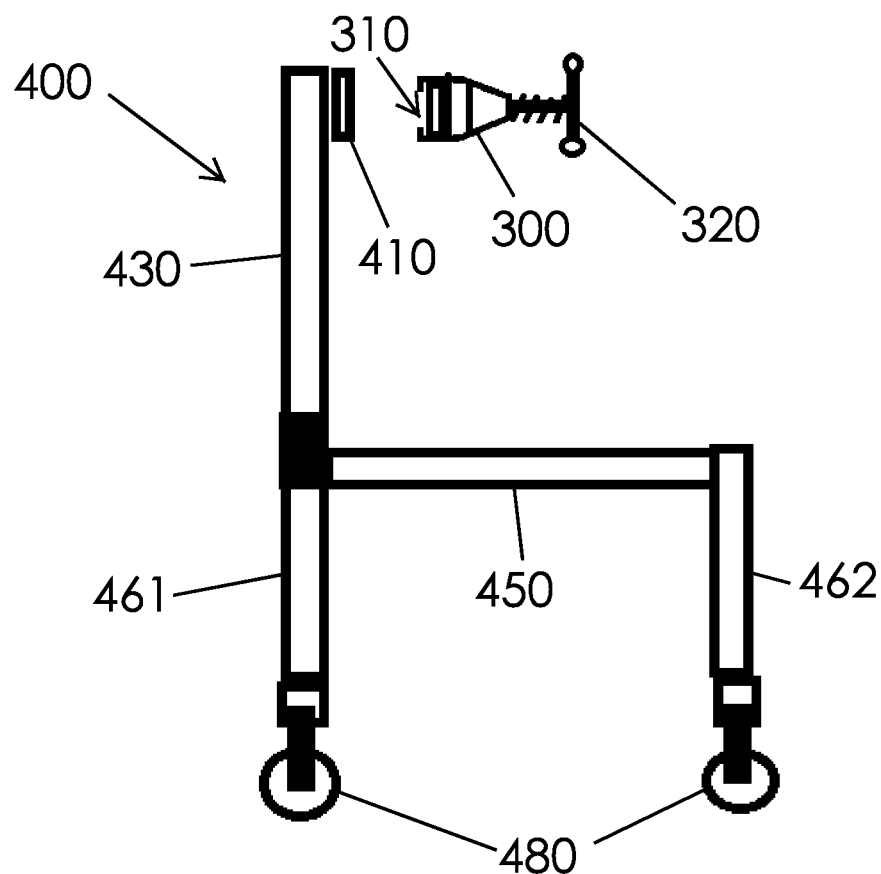
FIG. 38 is a front (back) view illustrating an exemplary portable base and an exemplary clamp.
Figure 39:
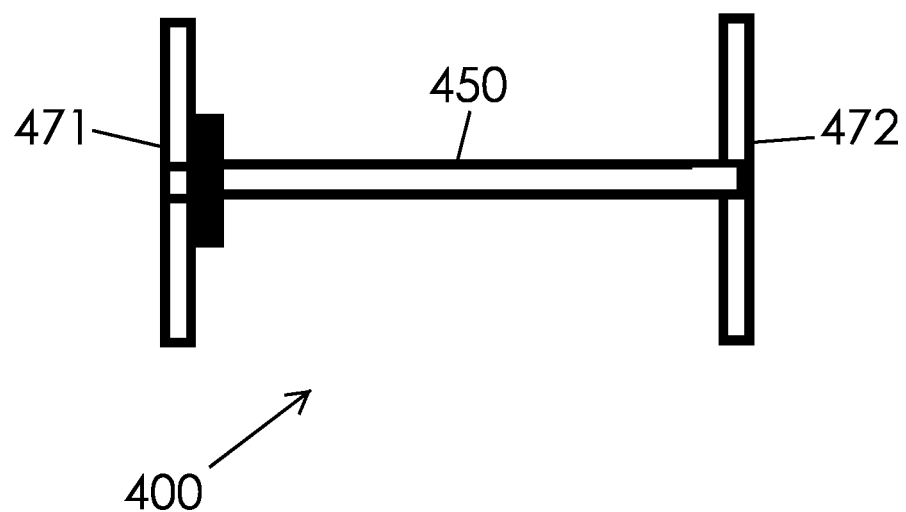
FIG. 39 is a top view illustrating the base of FIG. 38.

In accordance with some embodiments of the present invention, and as illustrated, for example, in FIGS. 38-43, a portable base 400 may be provided which may allow a user to portably move shield assembly 200 (e.g., for when a shield assembly cannot be engaged with a table). A base may generally comprise a plurality of elongated members, arms, or crossbars, or the like, which may be unitarily formed or connected together using a plurality of fasteners and/or welds, or the like. One or more of the crossbars may be oriented in an upright position (relative to a reference point, such as the ground) and may be configured to be engaged with a stand of a shield assembly. For example, as further illustrated in FIG. 38, portable base 400 may have a first upright crossbar 461 and a second upright crossbar 462, which may be disposed at opposite sides of portable base 400. Disposed between first upright crossbar 461 and second upright crossbar 462, and engaged therebetween, may be a medial crossbar 450. As illustrated in FIG. 39, disposed at a first lateral side of portable base 400 may be a first lateral crossbar 471 which may be engaged with first upright crossbar 461. Disposed at a second lateral side of portable base 400 may be a second lateral crossbar 472 which may be engaged with second upright crossbar 462. In some embodiments, one or more wheels may be engaged with a base. For example, as further illustrated in FIGS. 38 and 40-43, a plurality of wheels 480 may be engaged with first lateral crossbar 471 and second lateral crossbar 472, wherein, according to some embodiments, a pair of wheels may be engaged with each lateral crossbar.

Figure 40:
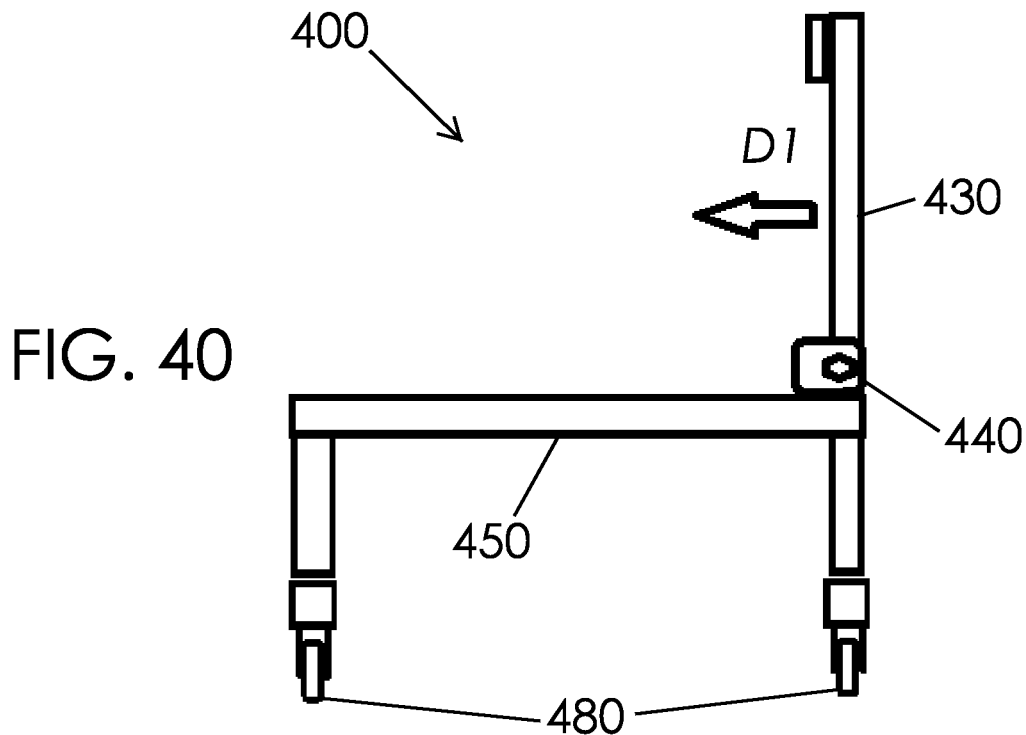
FIG. 40 is a back (front) view illustrating the base of FIG. 38.

According to some embodiments, a base may comprise an arm disposed at a lateral side of the base which may be used to anchor a shield assembly. For example, as illustrated in FIGS. 38 and 40, portable base 400 may comprise an arm 430 disposed at the first lateral side of portable base 400 and which may extend upward (i.e., away from lateral crossbars 471 and 472). In some embodiments, a base may comprise a hinge which may be configured such that an arm or crossbar may be pivoted thereon. For example, and as illustrated in FIG. 40, a hinge 440 may be disposed near an end of medial crossbar 450, wherein a lower end of arm 430 may be engaged to hinge 420. Arm 430 may pivot at the engagement point with hinge 440 in a direction indicated by D1, allowing arm 430 to be pivoted from an upright position to a position generally parallel with medial crossbar 450.

Figure 41:
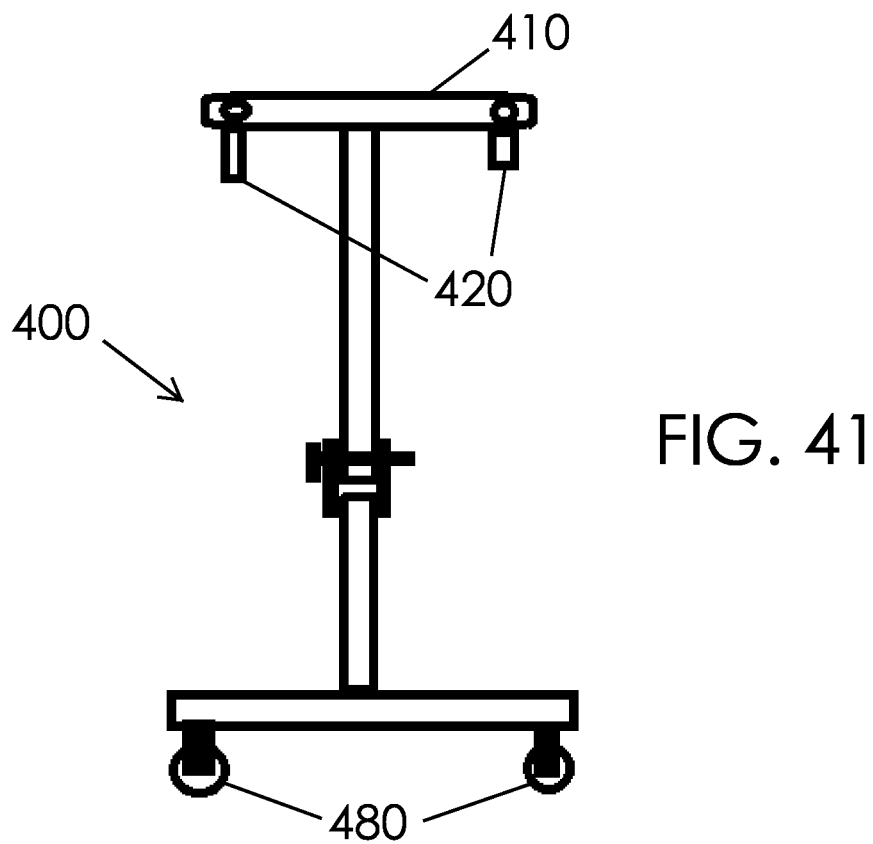
FIG. 41 is a side view illustrating the base of FIG. 38.

Engaged with arm 430 may be a rail 410 (see, e.g., FIG. 38) which may be generally orthogonal to arm 430. In some embodiments, an arm may comprise a securing member which may be slidable along the arm and which may be provided for securing a stand of a shield assembly to a base via an anchoring means. For example, as illustrated in FIG. 38, a clamp 300 may be configured to anchor stand 250 (not illustrated) of shield assembly 200 to portable base 400. Clamp 300 may comprise a bracket 310 for engaging rail 410 and securing thereto. In some embodiments, one or more tabs, protrusions, or other obstructions may be provided on a rail to prevent or limit movement of a clamp along the rail. For example, as illustrated in FIG. 41, tabs 420 may be disposed near each end of rail 410 and which may be configured to prevent clamp 300 from sliding off of rail 410 at either end thereof.

A clamp may generally have an opening or slot therethrough for receiving a stand of a shield assembly. In some embodiments, an opening or slot in a clamp may be pivotable, allowing a stand to pivot while secured within the clamp. As further illustrated in FIG. 38, clamp 300 may also comprise a handle 320 which may be configured to tighten or loosen clamp 300. For example, when stand 250 is received within an opening of clamp 300, handle 320 may be turned until stand 250 is secured within clamp 300. While engaged with clamp 300, shield assembly 200 may be pivoted such that stand 250 may be moved from a generally upright position, to a relatively diagonal position. Shield assembly 200 may also be rotated laterally such it may pivot around a longitudinal axis aligned with stand 250. For example, as illustrated in FIGS. 42 and 43, shield 220 may be rotated such that it may be generally aligned with a side of portable base 400 (when, for example, the shield assembly is not in use).

Figure 44:
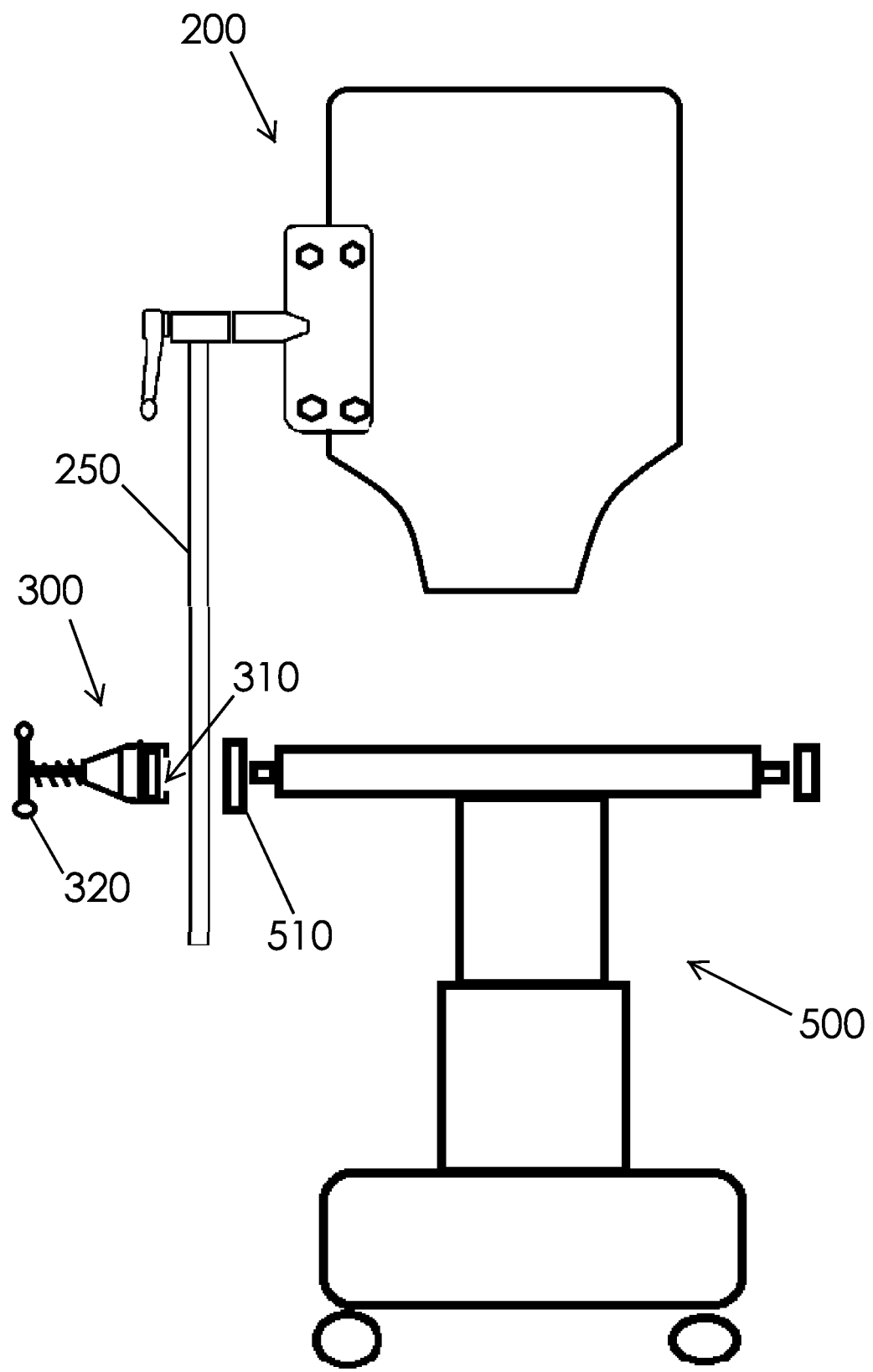
FIG. 44 is a front (back) view illustrating the shield assembly of FIG. 32, the clamp of FIG. 39, and an exemplary medical table.

In accordance with some implementations of the present invention, a shield assembly may also be used with a table, bed, or gurney, or the like (and which may be movable or fixed). For example, as illustrated in FIG. 44, shield assembly 200 may be engaged with a table 500 using clamp 300. Bracket 310 of clamp 300 may be configured to be engaged with a rail 510 of table 500. Shield assembly 200 may be engaged with table 500 by engaging clamp 300 (via bracket 310) with rail 510, inserting a portion of stand 250 into an opening in clamp 300, and tightening clamp 300 using handle 320.

It is to be understood that variations, modifications, and permutations of embodiments of the present invention may be made without departing from the scope thereof. It is also to be understood that the present invention is not limited by the specific embodiments, descriptions, or illustrations or combinations of either components or steps disclosed herein. Thus, although reference has been made to the accompanying figures, it is to be appreciated that these figures are exemplary and are not meant to limit the scope of the invention.

Moreover in this document, relational terms, such as second, top and bottom, and the like may be used solely to distinguish one entity or action from another entity or action without necessarily requiring or implying any actual such relationship or order between such entities or actions. The terms "comprises", "comprising", "has", "having,"

"includes", "including", "contains", "containing", or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises a", "has . . . a", "includes . . . a", "contains . . . a" does not, without more constraints, preclude the existence of additional elements of the same type in the process, method, article, or apparatus that comprises, has, includes, contains the element. The terms "a" and "an" are defined as one or more unless explicitly stated otherwise herein. The terms "substantially", "essentially", "approximately", "about", or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed. Also, the term "exemplary" is used as an adjective herein to modify one or more nouns, such as embodiment, system, method, device, and is meant to indicate specifically that the noun is provided as a non-limiting example.

What is claimed is:

1. A shield assembly comprising:
   a. a shield;
   b. a first support plate engaged with a first side of said shield and a second support plate engaged with a second side of said shield;
   c. a stand comprising a pivot;
   d. a rod engaged with said first support plate and pivotally engaged with said stand; and
   e. a lever arm engaged with a fastener;
   wherein a portion of said shield is disposed between said first support plate and said second support plate,
   wherein said fastener is disposed through an opening in said pivot and an opening in said rod, and
   wherein said shield is rotatable around a first axis centrally aligned with said opening of said pivot.

2. The shield assembly of claim 1, further comprising a clamp configured for engaging said shield assembly to a medical table, wherein a portion of said stand is received in an opening of said clamp.

3. The shield assembly of claim 2, wherein said stand is pivotally engaged with said clamp.

4. The shield assembly of claim 3, wherein said shield is pivotable around a second axis centrally aligned with said opening of said clamp.

5. The shield assembly of claim 4, wherein said stand is pivotable around a third axis orthogonal to said second axis.

6. The shield assembly of claim 1, further comprising a collar, wherein a portion of said stand is received through an opening in said collar.

7. The shield assembly of claim 1, wherein said shield comprises a first cut-out and a second cut-out, wherein said first cut-out and said second cut-out are each formed in a corner of said shield.

8. The shield assembly of claim 1, wherein a portion of said shield is disposed between a distal end of said first support plate and a distal end of said second support plate and wherein a lateral edge of said shield is disposed at about a longitudinal midpoint of each of said first support plate and said second support plate.

9. The shield assembly of claim 8, wherein said second support plate comprises a notch at a proximal end and aligned with said rod.

10. The shield assembly of claim 8, further comprising a slot between said first support plate and said second support plate, wherein said slot is disposed between a proximal end of each of said first support plate and said second support plate.

11. The shield assembly of claim 10, further comprising a plurality of spacers disposed within said slot.

12. The shield assembly of claim 1, wherein said pivot and said fastener are coupled with a spring.

13. A system for protecting a physician from airborne droplets produced by a patient, comprising:
   a. a shield assembly comprising a i) shield, ii) a first support plate engaged with a first side of said shield, iii) a second support plate engaged with a second side of said shield, and iv) a stand comprising a pivot; and
   b. a clamp comprising a handle, an opening, and a bracket;
   wherein said first support plate is pivotally engaged with said pivot of said stand,
   wherein a portion of said stand is received within said opening of said clamp,
   wherein said shield is rotatable around a first axis centrally aligned with an opening of said pivot,
   wherein said shield is pivotable around a second axis centrally aligned with said opening of said clamp, and
   wherein said stand is pivotable around a third axis orthogonal to said second axis.

14. The system of claim 13, further comprising a medical table, wherein said shield assembly is engaged with said medical table by said clamp.

15. The system of claim 14, wherein said medical table comprises a rail and wherein said bracket of said clamp is connected to said rail.

16. The system of claim 13, further comprising a portable base, wherein said shield assembly is engaged with said base by said clamp.

17. The system of claim 16, wherein said base comprises a rail and wherein said bracket of said clamp is attached to said rail.

18. The system of claim 17, wherein said base comprises one or more tabs for limiting the movement of said bracket along said rail.

19. The system of claim 16, wherein said base comprises a plurality of elongated members.

20. The system of claim 19, wherein said base comprises a hinge and wherein at least one of said elongated members is pivotally engaged with said hinge.

21. The system of claim 13, wherein said shield assembly further comprises a collar and wherein a portion of said stand is received through an opening in said collar.

22. The system of claim 19, wherein said elongated members comprise an arm, a medial crossbar, a first upright crossbar, a second upright crossbar, a first lateral crossbar, and a second lateral crossbar, wherein said arm is connected to said medial crossbar, wherein said first upright crossbar and said second upright crossbar are each connected to said medial crossbar, wherein said first lateral crossbar is connected to said first upright crossbar, and wherein said second lateral crossbar is connected to said second upright crossbar.

23. The system of claim 19, wherein said base comprises a plurality of wheels engaged with at least one of said elongated members.

24. A shield assembly comprising:
   a. a shield comprising a first cut-out and a second cut-out;
   b. a first support plate engaged with a first side of said shield and a second support plate engaged with a second side of said shield, wherein a portion of said shield is disposed between said first support plate and said second support plate and wherein a lateral edge of said shield is disposed at about a longitudinal midpoint of each of said first support plate and said second support plate;
   c. a stand comprising a pivot, wherein said pivot comprises an opening and wherein said shield is rotatable around a first axis centrally aligned with said opening of said pivot;
   d. a rod engaged with said first plate and pivotally engaged with said stand;
   e. a lever arm engaged with a fastener, wherein said fastener is disposed through said opening in said pivot and an opening in said rod; and
   f. a plurality of spacers disposed within a slot between a proximal end of each of said first support plate and said second support plate.

* * * * *